(12) United States Patent
Gomes et al.

(10) Patent No.: US 10,543,859 B2
(45) Date of Patent: Jan. 28, 2020

(54) RAILWAY WHEELS MONITORING SYSTEM AND METHOD

(71) Applicant: VALE S.A., Rio de Janeiro (BR)

(72) Inventors: Ana Claudia Da Silva Gomes, Belèm (BR); Cleidson Ronald Botelho De Souza, Belèm (BR); Adan Salazar Garibay, Irapuato (MX); Andres Hernandez Gutierrez, Tepic (MX)

(73) Assignee: VALE S.A., Rio de Janeiro (BR)

( * ) Notice: Subject to any disclaimer, the term of this patent is extended or adjusted under 35 U.S.C. 154(b) by 73 days.

(21) Appl. No.: 15/886,545

(22) Filed: Feb. 1, 2018

(65) Prior Publication Data
US 2018/0222499 A1     Aug. 9, 2018

(30) Foreign Application Priority Data

Feb. 2, 2017   (BR) .......................... 102017002219-6

(51) Int. Cl.
| | |
|---|---|
| *G06K 9/00* | (2006.01) |
| *H04N 7/18* | (2006.01) |
| *B61K 9/12* | (2006.01) |
| *G06T 7/62* | (2017.01) |
| *G06T 7/80* | (2017.01) |
| *H04N 13/204* | (2018.01) |
| *G06T 7/00* | (2017.01) |
| *G06T 19/20* | (2011.01) |

(52) U.S. Cl.
CPC ............ *B61K 9/12* (2013.01); *G06K 9/00771* (2013.01); *G06T 7/001* (2013.01); *G06T 7/62* (2017.01); *G06T 7/85* (2017.01); *G06T 19/20* (2013.01); *H04N 13/204* (2018.05); *G06T 2207/10012* (2013.01); *G06T 2207/30164* (2013.01)

(58) Field of Classification Search
USPC ........ 382/100, 103–104, 106–108, 120–123, 382/154, 168, 173, 181, 199, 209, 219, 382/254, 276, 285–291, 305, 317; 348/148; 701/31.4; 246/169
See application file for complete search history.

(56) References Cited

U.S. PATENT DOCUMENTS

| | | | |
|---|---|---|---|
| 8,925,873 B2 * | 1/2015 | Gamache ................. | B61K 9/12 246/169 R |
| 2009/0055043 A1 * | 2/2009 | Mian ................... | B61L 27/0094 701/31.4 |
| 2010/0100275 A1 * | 4/2010 | Mian ................... | G01M 17/013 701/31.4 |
| 2014/0285658 A1 | 9/2014 | Mian et al. | |

(Continued)

*Primary Examiner* — Seyed H Azarian
(74) *Attorney, Agent, or Firm* — Arent Fox LLP (57) ABSTRACT

It is described a system and method to monitor railway wheels, which includes obtaining images of the railway wheel by means of stereo cameras and performing a three-dimensional and two-dimensional model of the railway wheel by means of these images. This two-dimensional model is subjected to analysis of the profile of the railway wheel, comparing it with a two-dimensional model of an ideal wheel and thus measuring the effective wear of its profile. The three-dimensional model is subjected to analysis of the surface of the railway wheel, also comparing it with a three-dimensional model of an ideal wheel and thus measuring the effective wear of its surface.

18 Claims, 4 Drawing Sheets

(56) References Cited

U.S. PATENT DOCUMENTS

| | | | |
|---|---|---|---|
| 2015/0369701 A1* | 12/2015 | Graf | G01B 11/16 |
| | | | 382/104 |
| 2016/0059623 A1* | 3/2016 | Kilian | G01B 11/2408 |
| | | | 348/148 |
| 2016/0282108 A1* | 9/2016 | Martinod Restrepo | B61K 9/12 |

* cited by examiner

Step 17

Figure 5

Step 18

RAILWAY WHEELS MONITORING SYSTEM AND METHOD

CROSS REFERENCE TO RELATED APPLICATION

This application claims priority to BR Application No. 102017002219-6 filed Feb. 2, 2017, the disclosure of which is hereby incorporated by reference in its entirety.

FIELD OF THE INVENTION

The present invention relates to a system and method for monitoring of railway wheels.

BACKGROUND OF THE INVENTION

Railway wheels consist of wheels used in vehicles that move on rails. Such vehicles are used, for example, for the transport of materials and people.

The most common vehicle to use this type of wheel is a railway train, which is interconnected to several cars classified according to what is being transported. When the train transports passengers, it is named passenger train; when transporting materials, it is named freight train.

Out of the aspects that are studied and analyzed in a railway system, the most important, and of interest, are: train derailment; maintenance costs; and efficient logistics strategies.

Train derailment it is generally caused due to loss of friction between the railway wheels and the rails, causing the train to lose contact with these elements.

This loss of friction causes the train to get off the rails, causing accidents and severe damages due to the large dimensions and high mass of the train.

Regarding maintenance costs, the railway wheels/the rails interaction it plays a vital role not only in maintaining trains but also in fuel consumption, safety, and ride quality for passenger trains. Finally, a derailment potentially affects the logistics contract, which may have financial implications due to loss of cargo or even loss of life resulting from rail accidents.

The main causes of train derailment are: wheels/rails interaction, broken rails, weld failures, rail geometry imperfections, rail gauge failure, and broken wheels.

All factors cited after "wheels/rails interaction" also resulting from this same phenomenon. In other words, broken rails, gauge failure, rail geometry, and weld failure may directly or indirectly affect the "wheels/rails interaction". To name one example, a damaged railway wheels profile can cause rail geometry failures and surface imperfections, which in turn lead to excessive wheel wear.

Therefore, it is of great interest and importance to design and use a monitoring system and method for railway wheels that prevents accidents due to poor wheel condition or wheels/rails interaction failures.

In the state of the art, such monitoring is periodically performed, and the operation of the train and its cars must be stopped in order to verify the rail wheels.

Such verification is manually performed by one or more workers, who walk along the train checking its wheels and identifying which ones are excessively worn and need to be replaced.

However, this method requires a very long execution time and is subject to human failures, since the verification is manually performed by the workers. Furthermore, because verifications occur in a periodic basis, there is a great risk of a wheel suffering excessive wear or deformation over the period between verifications.

The state of the art also comprises some documents that disclose a monitoring of railway wheels, and they are described below.

A document comprising the state of the art is U.S. Pat. No. 8,925,873, which discloses a device and method for measuring and verifying dimensions related to wear of wheels on rails. This device consists of fast actuation cameras associated with laser meters, configured to construct a model of the wheel and thus verify dimensions such as angle of attack, wheel misalignment, and other dimensions that are related to premature wear of this element.

The application of the device and method of U.S. Pat. No. 8,925,873 allows verifying the premature wear of the wheels and decrease the number of necessary maintenances, avoiding accidents caused by the premature wear of these elements.

In U.S. Pat. No. 8,925,873 the device is installed on both sides of each rail to perform a partial modeling of the wheel or truck (combination of two wheels with an axle) of the equipment. The images captured by the camera and the laser sensors are obtained during the passage of the train, and it is not necessary to stop the train to perform measurement.

The images obtained by the cameras are then subjected to triangulation with the lasers to generate an accurate image of the wheel and read its dimensions.

However, said method allows only a measurement of the wheels by means of the images obtained by the device, not being possible to compare them with other wheels in perfect condition or with an ideal wheel model to determine the effective wear of the wheel.

The method described in the American document also does not allow to verify dimensions not captured by the cameras or sensors, such as the surface of wheels that is in contact with rails, making it impossible to check for anomalies in this section of the wheel and verify the wheel/rail interaction.

Moreover, the device does not allow using only cameras, requiring the application of laser sensors to perform the modeling of the wheel being monitored, thus increasing the cost of the device.

Another document of the state of the art is patent application US20140285658, which discloses a method and device for measuring wheels on rails without contact with the wheels. The device consists of cameras and laser sensors, installed near the rail or operated by an operator, configured to capture images of the wheel. The device can also be combined with a position sensor for greater accuracy when mounting each image.

The device of US20140285658 allows capturing the wheel in whole or only a section of interest. When a wheel is captured in whole, a three-dimensional model of the wheel is made by a computer system, configured to process the images obtained by the cameras and lasers.

In the computer system described in US20140285658, it is possible to perform several types of wheel measurement, thus allowing verification of the dimensions of most of its components. In addition, the system also comprises an option of comparing a first three-dimensional model with other models obtained by the same device to check for possible wheel anomalies and deformations.

However, such device and method do not allow measuring the surface of the rail wheel, only measuring the wheel profile, preventing the identification of deformations on the wheel surface, such as protrusions, surface irregularities, and other types of problems. Since it does not allow measuring the wheel surface, the method described also prevents the verification of the wheel/rail interaction, which can generate direct costs such as accidents and indirect costs such as excessive fuel consumption and passenger discomfort.

Furthermore, the method disclosed in US20140285658 only allows comparison of the wheel models measured by the device with other wheel models also obtained by the device, being not possible to introduce an ideal wheel model to measure the effective wear of the wheel.

Thus, it is concluded that both the periodic technique of monitoring rail wheels and the devices and systems disclosed in the state of the art are not able to effectively verify the wheel surface, thus preventing the verification of the wheel/rail interaction.

Further, none of the devices, systems, and methods in the state of the art are capable of measuring effective wear of the wheel surface and profile, comparing it with an ideal wheel model.

OBJECTS OF THE INVENTION

The present invention aims at a system to monitor railway wheels that allows measuring and analyzing their profile and surface.

The present invention also aims at a method for measuring the effective wear suffered by a monitored railway wheel by means of comparison with an ideal railway wheel model.

BRIEF DESCRIPTION OF THE DRAWINGS

The present invention is detailed described based on the respective figures.

DETAILED DESCRIPTION OF THE INVENTION

The present invention describes a system and method for the monitoring of railway wheels 5. Such monitoring makes it possible to visualize and analyze both the wheel profile 5 and its surface 3.

In addition, monitoring also allows analyzing the entire profile and surface 3 of the railway wheels 5, comparing it with an ideal wheel model to measure its effective wear.

Monitoring can be divided into three fundamental steps: measuring the profile 17 of the wheel 5; analyzing the profile 18 of the wheel 5; and analyzing the surface 19 of wheel 5.

The first aspect relates to the provision of measurements relative to the geometry of the wheel 5. Regarding the analysis of the profile 18 of the wheel 5, in this step its geometry is analyzed along its entire profile, and this profile is generated only with two dimensions (2D).

The analysis of the surface 19 of the wheel 5 involves extending this process along the profile of the wheel 5 (2D) to a small region of the surface 3 of the railway wheels 5, thus obtaining a three-dimensional (3D) model of the wheel 5, which is subjected to analysis.

This 2D-to-3D extension is of significant importance as allows understanding the wheel 5/the rail 4 interaction and the dynamics of the wheel 5 while moving along a railroad. Each of these monitoring steps is separately explained below.

Measurement of Wheel Profile (17)

The monitoring system uses two synchronized stereo cameras, preferably distributed as follows: one on each side of the rail 4, being the first stereo camera 8 and the second stereo camera 9 (refer to FIG. 1).

Each stereo camera 8 and 9 comprises two lenses, the first stereo camera 8 comprising the first left lens 6 and the first right lens 7, and the second stereo camera 9 comprising the second left lens 6' and the second right lens 7'.

Figure 1:
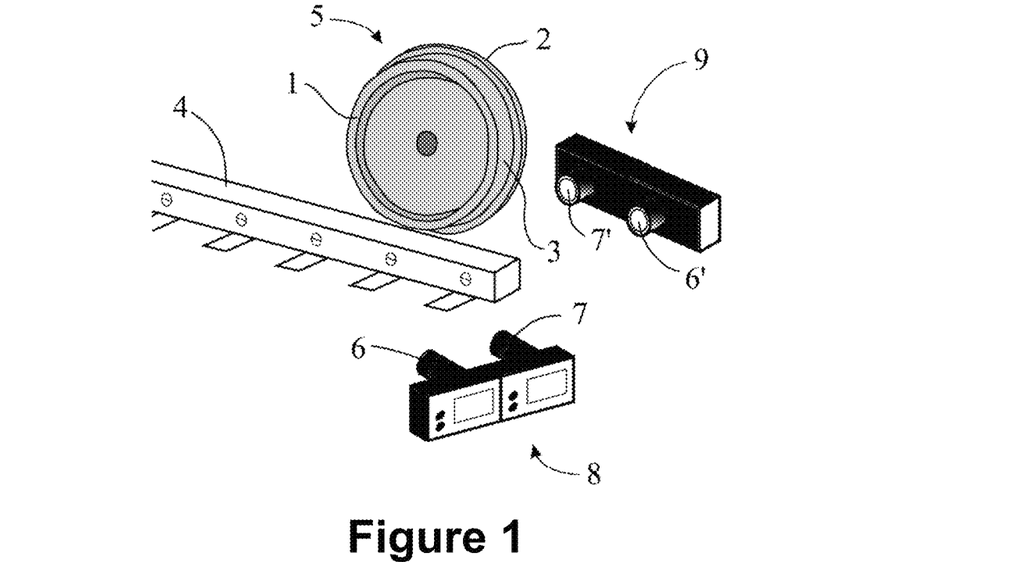
FIG. 1 is a perspective view of the preferred embodiment of the monitoring system of the present invention.

This distribution is used to capture a stereo image from both the outer side 2 and the inner side 1 of the railway wheel 5, refer to FIG. 1. Thus, the first stereo camera 8 captures images from the inner side 1 of the wheel 5, while the second stereo camera 9 captures images from the outer side 2 of the wheel 5.

These stereo images, along with each of the calibration parameters of camera 8 and 9, allow a 3D reconstruction of both sides 1 and 2 of the railway wheel 5.

Such 3D reconstruction is possible by applying the following pre-processing steps: correction of image distortion; image rectification; mapping; and calculation of image disparity.

The correction of image distortion uses the calibration parameters 11 of each stereo camera 8 and 9 (refer to FIG. 2) to compensate for lens distortions 20 and 21 so that straight lines in the real world are presented as straight lines the mapped image Image rectification ensures that an image component detected on a given line of the stereo image is on the same line of the mapped image.

Mapping and calculation of image disparity maps the distance between corresponding pixel points in the rectified images to a metric depth in order to calculate the three-dimensional distance of the left lens relative to the subject.

The system calculates the disparity map using either the stereo block matching algorithm (BlockMatching) or the stereo semi-global block matching algorithm (Semi-Global Matching). Both algorithms aim to determine the corresponding points between the stereo images. This determination is performed by comparing the pixel intensity values of the two images where the smallest absolute difference is chosen by determining the matching point. The last step required for 3D reconstruction is triangulation. This method combines the disparity map and the distance between the two lenses to estimate the three-dimensional position of a measured object relative to the left lens of the stereo camera.

In other words, since the distance between the two lenses of a stereo camera remains the same for any captured object, the value attributed to this distance is precisely known to its developer, one just need to compare the differences of these images obtained by the two lenses and consider the distance between the two lenses in the calculation to determine the distance between one of the lenses and the captured object.

After applying these pre-processing steps for both stereo images of the inner side 1 and the outer side 2 of the railway wheel 5, the system is capable of performing three-dimensional (3D) reconstruction 13 and 13' of each side 1 and 2, corresponding to the railway wheel 5.

This process is followed by the step of recording the points in the three-dimensional cloud. This step combines the two 3D reconstructions in order to produce a single three-dimensional model of the railway wheel 5, named observed model, using the iterative closest point algorithm (ICP) and the extrinsic calibration parameters of the two stereo cameras 8 and 9. The ICP is an algorithm used to record point clouds and aimed at, by means of an iterative process, a transformation that minimizes the difference between two point clouds During its execution, a point cloud named reference is kept fixed, while the other point cloud is iteratively transformed until it finds the nearest corresponding point of the reference cloud.

Figure 5:
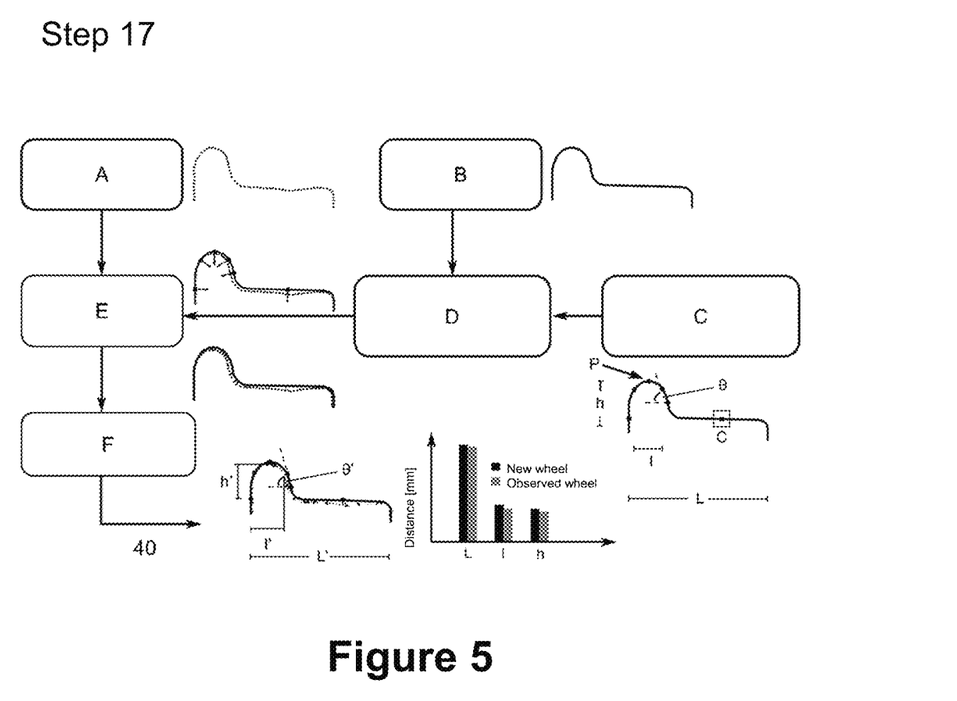
FIG. 5 depicts a flowchart of the steps involved in measuring the railway wheel profile.

Measuring the wheel profile 17, based on the use of a theoretical 2D model B of a railway wheel 5, aims at the measurement of particular parameters of the geometry of the wheel 5 such as: flange width I, flange height h, flange angle θ, wheel width L (refer to FIG. 5).

This is made possible by comparing the theoretical 2D model B of the railway wheel 5, named "real model", with a profile of the observed 2D model that is obtained in the three-dimensional reconstruction of the railway wheel 5 using the stereo cameras, named "observed model".

This comparison is based on the calculation of the distance of function points, located in fixed coordinates along these two wheel profiles.

By providing a theoretical 2D model B of the railway wheel 5, which can be obtained from the manufacturer of the wheel 5, this approach can be adapted to any type of railway wheel 5.

Analysis of Wheel Profile (18)

Unlike the measurement step of the profile 17 of the wheel 5, which measures particular features of the geometry of a railway wheel 5, the analysis of the wheel profile 18 aims to provide a solid understanding of how the wheel 5 has been used along it profile.

To perform this measurement, all points along the real model are compared to their corresponding points in the observed model. After this comparison, the estimated effective wear of the wheel along its profile is calculated by calculating the Euclidean distance between each point in the theoretical or real 2D model B and its corresponding point located in the observed 2D model A. The Euclidean distance is a measure of dissimilarity between two points, the larger this measure, the smaller the similarity between the points.

Thus, it is possible to determine how close the points of the observed model are to the points of the theoretical model.

Figure 6:
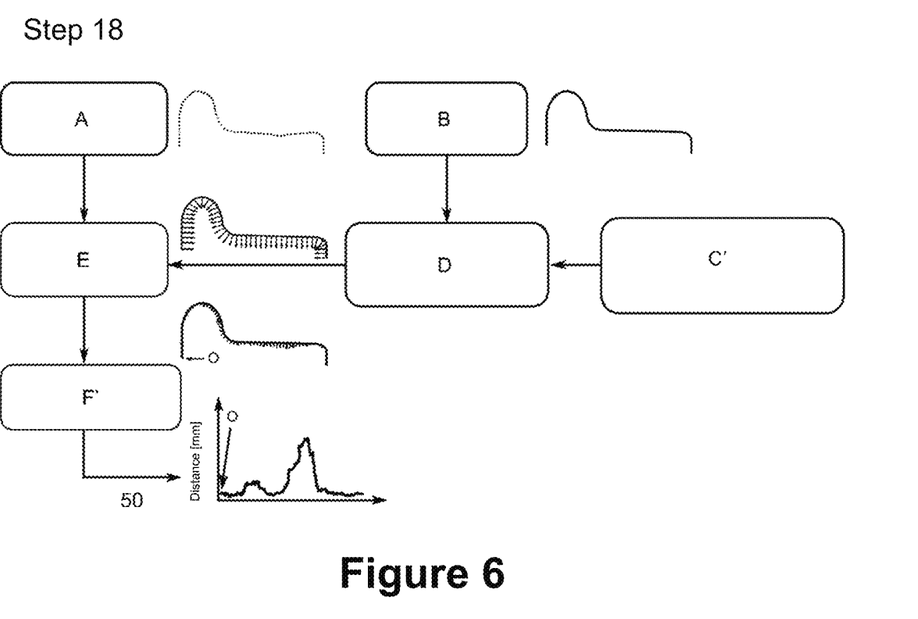
FIG. 6 depicts a flowchart of the steps involved in analyzing the railway wheel profile.

Since this analysis is performed along the wheel profile, the monitoring system produces a curve 50 of the Euclidean distance provided by the real and observed models.

By means of this curve 50, it is possible to estimate the effective wear of the profile of the railway wheel 5, refer to FIG. 6. The resolution of the resulting curve 50 depends on the resolution of the observed 2D model A, which basically depends on the combined resolution of the two stereo cameras 8 and 9. That is, the better the resolution of the 8 and 9 cameras, the more accurate is the estimated wear on the profile of the railway wheel 5.

Analysis of Wheel Surface (19)

An additional and fundamental feature of the monitoring system is to estimate the wear of the surface region 3 of the wheel 5, which corresponds to the area of contact with the railway 4.

Such surface area 3 is defined by said region of the railway wheel 5 appearing in the combined field of view of the two stereo cameras 8 and 9, that is, the region which is not integrally captured by them.

In this case, the system calculates the Euclidean distance between the points belonging to the real model and the points in the model observed for the region specified in the surface area 3 of the wheel 5.

This method 19 and the profile analysis method 18 allow understanding the wheel 5/rail 4 interaction, thereby performing a more thorough analysis of the wheel 5 using some of the parameters of the wheel 5 measured in the first step 17. This procedure is of great importance for the prevention of train derailment and reduction of fuel consumption.

Figure 2:
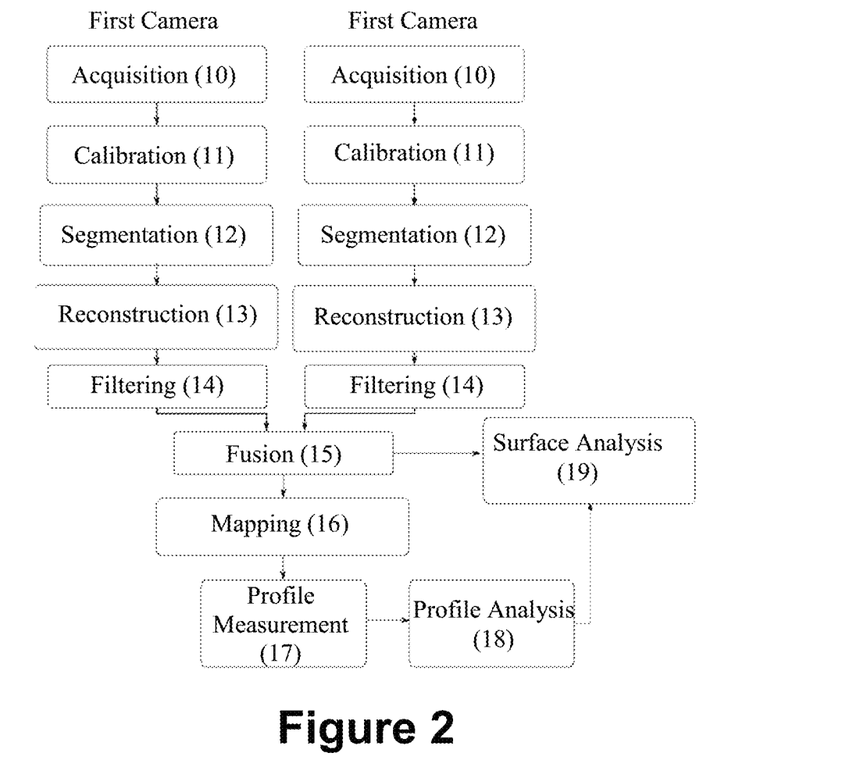
FIG. 2 depicts a block diagram of the steps involved in monitoring the railway wheel in the preferred embodiment of the present invention.

Details of the three main aspects disclosed above (profile measurement 17, profile analysis 18, and surface analysis 19) and the complete process of measuring and analyzing the geometric characteristics of the profile of the wheels 5 are disclosed in a block diagram in FIG. 2, where the following steps are described: acquisition of the stereo image 10; correction of image distortion or calibration of the stereo cameras 11; segmentation of the railway wheel 12; 3D reconstruction of inner side 1 of the wheel 13; reconstruction of the outer side 2 of the wheel 13'; 3D data filtering 14; 3D data fusion 15; mapping of the three-dimensional model 16; measurement of the railway wheel profile 17; analysis of the railway wheel profile 18; and analysis of the railway wheel profile 19.

Having described the three main aspects that comprise the railway wheel 5 monitoring system, the following are the configurations and order of execution of each step that comprise the method of monitoring railway wheels 5.

The first step 10 consists of the acquisition of the stereo image of the railway wheel 5, preferably using two stereo cameras 8 and 9. Each stereo camera is placed on either side of the rail 4, as shown in FIG. 1.

1. The cameras in the present invention are named the first stereo camera 8 and the second stereo camera 9, respectively. Each camera comprises a pair of lenses arranged in parallel having competing fields of view, the first camera 8 comprising the first left lens 6 and the first right lens 7, and the second camera 9 comprising the second left lens 6' and the second right lens 7'.

Alternatively, laser sensors or lights designed to aid in the acquisition of images of the wheels may be used and integrated into the stereo cameras 8 and 9.

The frame rate for acquisition of stereo images can be previously configured so that it is ensured that each wheel 5 belongs to a certain car that fits within the field of view of the stereo cameras 8 and 9. Thus, when a train or car moves around the place where the cameras 8 and 9 are installed, they capture the stereo image 10 of all the wheels 5 that comprise the vehicle, allowing to separately analyze each wheel 5.

The distance, geometry, and orientation of each stereo camera 8 and 9 relative to the rail 4 must be defined according to the technical specifications of the cameras 8 and 9, as well as the lighting conditions and vibrations produced by the movement of the vehicle and along the rail 4.

The second step 11 consists of calibrating the stereo cameras 8 and 9 to compensate for the distortions occurring on the lenses 6, 6', 7, and 7' of these elements. There are two different types of distortion that occur in most cameras: radial distortion 20 and tangential distortion 21 (refer to FIGS. 7 and 8). Both distortions 20 and 21 are due to the lens manufacturing and installation process.

Figure 7:
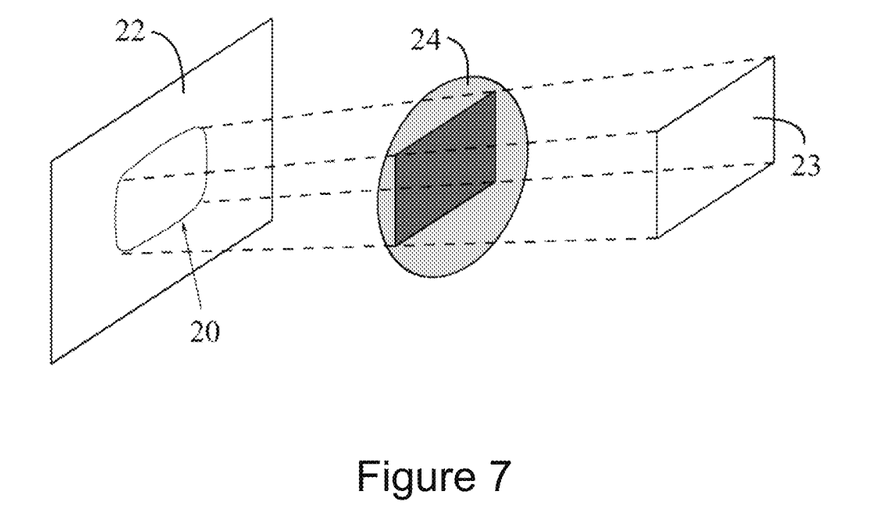
FIG. 7 depicts an example of radial distortion caused by the lens of a conventional camera.

Radial distortion 20 is generated by the fact that it is always easier and cheaper for the lens manufacturer to manufacture a spherical lens than an ideal parabolic lens. This feature present in the lens manufacturing process causes the spherical lens to generate this distortion 20 (refer to FIG. 7). In FIG. 7, it is possible to see a distorted image 20 in the image plane 22, caused by the lens 24 when it is interposed to the object 23.

Figure 8:
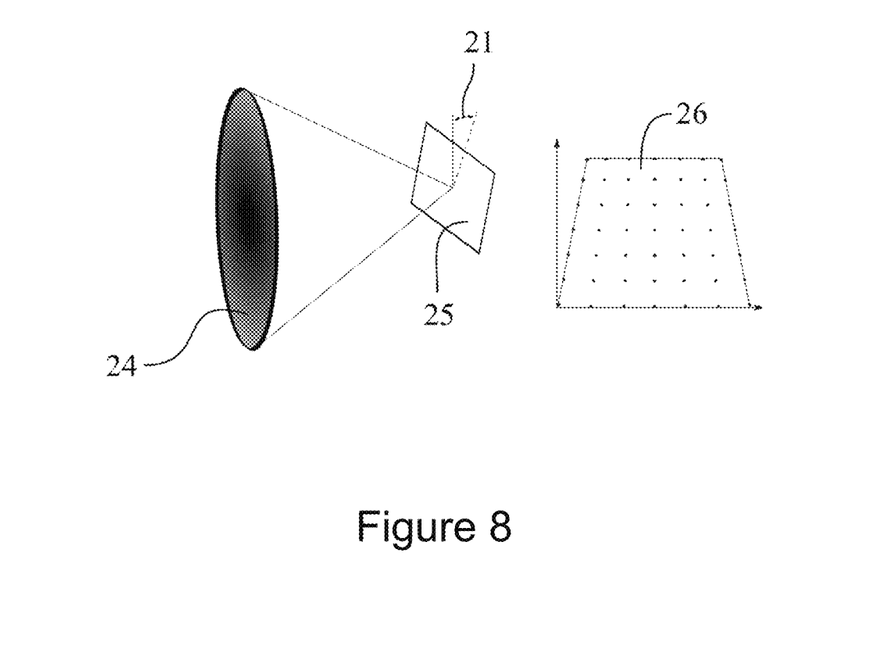
FIG. 8 depicts an example of tangential distortion caused by the lens of a conventional camera.

Tangential distortion 21 is mainly related to the fact that it is of great difficulty to perfectly align the lens of the camera 24 with the sensor of the camera 25, refer to FIG. 8 that represents the lens of the camera 24 misaligned with the sensor of the camera 25 and the distorted image 26.

To perform a 2D or 3D measurement of an object, the effect of these distortions 20 and 21 on the captured stereo images must be corrected. This correction is done by means of a process named camera calibration 11. This process aims to estimate two types of parameter: intrinsic parameters and extrinsic parameters.

Intrinsic parameters refer to the direction of the rays to be spread by a 3D object through the optical center of coordinates in the image plane. The main intrinsic parameters to be estimated for each lens are: focal length, main point, inclination coefficients, and radial 20 and tangential distortions 21.

Figure 3:
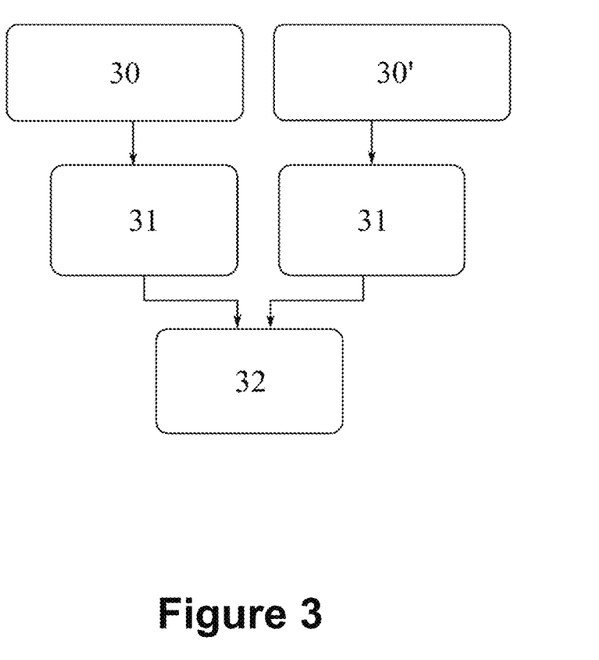
FIG. 3 depicts a block diagram of the calibration process of the stereo camera.

With respect to the extrinsic parameters, they encapsulate the position and orientation of the lenses of each stereo camera 8 and 9 that comprises the monitoring system. FIG. 3 depicts a block diagram of the calibration process, showing the following steps: acquisition of the left image 30; acquisition of the right image 30'; monocular calibration 31, performed using the intrinsic parameters; and stereo calibration 32, performed using the extrinsic parameters.

The third step 12 consists of the segmentation of the rail wheel, this step being configured to aid and streamline the fourth step, in which the rail wheel is reconstructed in a three-dimensional model 13 and 13'.

This segmentation calculation can use the pixels belonging to the rail wheel 5 photographed. The process of dividing pixels of an image into its constituent regions or objects is named segmentation. There are several techniques for image segmentation, in the present invention the adopted segmentation technique is based on the transformed distance.

Figure 4:
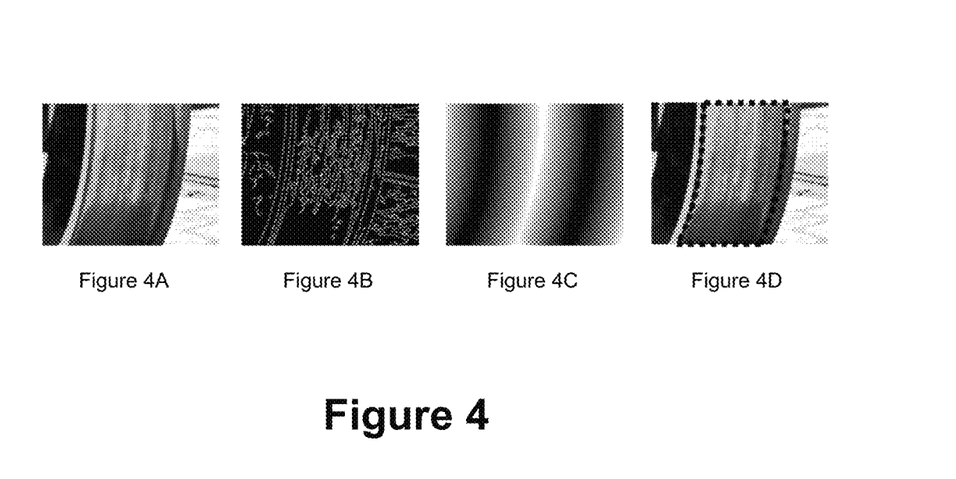
FIG. 4A shows the input image in the process of segmentation of the stereo image.
FIG. 4B shows the balanced corners in the process segmentation of the stereo image.
FIG. 4C shows the segmentation based on the transformed distance.
FIG. 4D shows the wheel finally segmented.

The results obtained using this technique are disclosed in FIG. 4. FIG. 4A shows the input image, FIG. 4B shows the balanced corners, FIG. 4C shows the segmentation based on the transformed distance, and FIG. 4D shows the wheel 5 finally segmented.

For the 3D reconstruction of a section of the rail wheel 5, generated by any of the stereo cameras 8 and 9, only the pixels within the dotted rectangle on the surface of the wheel 5 (shown in FIG. 4D) are considered by the 3D reconstruction algorithm.

The fourth step 13 and 13' of the flow chart in FIG. 2 consists of the reconstruction of a three-dimensional model of the wheel 5 subjected to the monitoring system. The reconstruction of the three-dimensional model is achieved using a triangulation process.

This process is based on the use of corresponding points that are detected both in the images obtained by the left lenses 6 and 6' and by the right lenses 7 and 7' of the stereo cameras 8 and 9, respectively. That is, for an element present in the segmented region in the left image, the corresponding pixel must be detected in the segmented region of the right image. This procedure is named corresponding resource.

Since each pixel is located at a given x and y coordinate, the x coordinates of the element in the left and right images are obtained, and the difference between these two pixels, named disparity, is used to calculate the three-dimensional location of the pixel relative to the left lens 6 by means of the triangulation process. This process is repeated for each pixel present in the segmented area of the rail wheel 5, thus allowing its complete reconstruction.

Steps 1 and 2, that is, acquisition of images 10 and calibration of stereo cameras 11, are required for each stereo camera 8 and 9 as shown in the block diagram of FIG. 2. Therefore, each stereo camera 8 and 9 produces a partial reconstruction of the rail wheel 5.

The first stereo camera 8 reconstructs the inner side 1 of the wheel while the reconstruction of the outer side 2 of the wheel is generated by the second stereo camera 9. These two three-dimensional reconstructions 13 and 13' may contain sparse groups of points (the noise) that must be removed prior to the application of the 3D data fusion algorithm, which is explained in the sixth step, in order to obtain complete reconstruction of the surface 3 of the rail wheel 5. This noise removal procedure is described below in the fifth step.

The fifth step 14 consists of the removal of distorted three-dimensional points, in other words, the removal of noise or filtering of 3D data, thus generating greater accuracy in the reconstructed 3D model.

In this step, taking into account the three-dimensional reconstructions 13 and 13' of each side 1 and 2 of the rail wheel 5, the sparse and distorted points are removed by means of a theoretical three-dimensional model of the surface 3 of the rail wheel 5.

The distance from each three-dimensional point to the surface 3 of the rail wheel 5 is used to classify a 3D reconstruction point as potentially belonging to the surface 3 of the wheel 5, that is, only points at plausible distances are considered for the reconstruction of the three-dimensional model of the wheel 5.

A statistical analysis is also performed in this process in order to achieve a robust form for the 3D data filtering process 14. Approaches to performing this statistical analysis include: linear regression, 2D and 3D curve adjustment, or grouping. The advantage of this step 14 is a 3D reconstruction free of noisy 3D points, making it easy to measure the characteristics of the wheel 5 in the next steps.

The sixth step 15 consists in the fusion of these three-dimensional points obtained by the previous steps. After provision of the two sets of 3D points representing the three-dimensional reconstruction 13 and 13' of each side 1, 2 of the railway wheel 5 free of noisy points, a 3D data fusion technique 15 is then applied.

To perform 3D data fusion 15, the method uses a three-dimensional data fusion algorithm. This algorithm takes into account the calibration information 11 of step 2 generated by computing the extrinsic parameters between the left lens 6 of the first camera 8 and the right lens 7' of the second camera 9.

These parameters encapsulate the relative translation and orientation between these two lenses 6 and 7'. Then the 3D points are subjected to a rigid transformation that allows the system to combine the 3D point cloud obtained by the second camera 9 with the 3D point cloud obtained by the left lens 6 of the first camera 8.

This combination allows the system to reproject these 3D point clouds in a 3D coordinate system. This is made by means of an iterative closest point algorithm (ICP, explained above in item Measurement of the Wheel Profile).

In this step, both reconstructions 13 and 13' are fused into a single representation so that a three-dimensional model of the rail wheel 5 is generated. This unique three-dimensional model of the rail wheel 5, named observed 3D model, is then used for the analysis of estimated wear of the wheel and wheel profile, as described in the next steps.

The seventh step 16 consists of mapping the three-dimensional model generated by the sixth step to an observed 2D model A. To generate the observed 2D model A for wheel profile analysis, the projected 3D coordinates (X, Y, Z) are associated with the coordinates generated by the theoretical 2D model B.

This association is made by overlapping the theoretical 2D model B with the observed 3D model (model reconstructed in the sixth step) to align both models and then performing a data association for the 3D points that are closest to the points of the theoretical 2D model B.

Thus, the seventh step is able to formulate the profile of the observed model, generating an observed 2D model A.

The eighth step 17 consists of measuring the profile of the railway wheel 5, which receives as input a theoretical 2D model B of a new railway wheel 5, and the observe 2D model A obtained in the seventh step.

FIG. 5 shows the components and procedures present in this step, being the observed 2D model A, the theoretical 2D model B, the set of path points C, the computation of normal vectors D, the association of data E, and the estimation of wheel characteristics F.

The set of path points C defines the characteristic points that facilitate the measurement of parameters of wheel profile geometry, such as flange height h, flange width I, flange angle θ, wheel width L, and other dimensions of interest. The location of these path points along the wheel profile is standardized and the coordinate of each point is performed based on the location of the highest point of flange P of the rail wheel 5.

Computation of normal vectors D calculates the internal normal vector of the reference points located along the profile of the observed 2D model A. The computation is done considering two consecutive points along the wheel profile and finding the equation of the straight line that unites these two points. Then, the inclination of this equation is inverted and used to determine the normal vector. The curve shown in the left portion of the computation of normal vectors D in FIG. 5 exemplifies the result of this operation.

Data association E compares points (of the point path) of the observed 2D model A with the corresponding points along the theoretical 2D model B, thus aligning the two 2D models, as shown below data association E in FIG. 5.

For a given point along the observed 2D model A, this procedure calculates its perpendicular distance in relation to the intersection of two closest normal vectors, comparing this distance obtained in the observed 2D model A and in the theoretical 2D model B to verify which perpendicular distance is smaller.

This data association process E is repeated for each point along the observed 2D model A in order to associate data to all points along the profile of the wheel 5.

The estimation of wheel characteristics F uses the corresponding points obtained from data association E, generating a new profile 40 that shows the new flange angle θ', the new flange height h', the new wheel width L', the new flange width I', and all characteristics of the rail wheel 5 subjected to measurement.

The ninth step 18 consists of the analysis of the 2D profile of the rail wheel 5 using parameters measured in the eighth step 17 to aid the analysis. In addition, the ninth step 18 is very similar to the eighth step 17. The only two differences are the set of path points C' and the estimation of wheel characteristics F', refer to FIG. 6.

The set of path points C' is now defined for all points indicated in the theoretical 2D model B, so that it is possible to analyze each point along the profile of the wheel 5.

Regarding the estimation of wheel characteristics F', its result is a curve 50 that shows the effective wear of the profile of wheel 5. The analysis of the profile 18 of the wheel 5 allows to discover where, from the wheel profile, the wheel is deteriorated compared to a new railway wheel 5.

In addition, this estimation allows to understand the wheel 5/rail 4 interaction, which in turn allows to design new wheel profiles, rails, and train parameter sets such as speed and acceleration, which can be used not only for increasing the service life of a wheel rail 5, but also reducing fuel consumption costs.

The tenth and final step 19 consists of analyzing the surface 3 of the railway wheel 5. In addition to estimating the degradation of the wheel 5 along its profile, the system can also analyze the surface 19 in 3D. To perform this analysis 19, the system takes into account the observed model generated in the sixth step 15 and some characteristics measured in the seventh step 17.

Two different approaches can be adopted to perform surface analysis 19, which are explained below.

The first approach consists of dividing the observed 3D model obtained in the sixth step 15 into several slices and applying the module of analysis of the 2D profile of the rail wheel 5, as described in the seventh step 16.

The second approach consists of performing a correspondence of pairs of three-dimensional points between the points of the observed 3D model and the theoretical 3D model. This theoretical 3D model can be a surface of revolution of the theoretical 2D model B, which can basically be obtained by aligning a theoretical 2D model B with the observed 3D model and rotating it with respect to the center of the rail wheel 5.

Once these two 3D models are aligned, the pairs of points associated in 3D from the observed model can be associated with those of the theoretical 3D model, using the nearest neighbor algorithm.

The parameter used to measure the distance between the two points can be the Euclidean distance or the Mahalanobis distance. In the first case, the uncertainty in the 3D point position is not taken into account, making this second approach more robust for noisy data.

Thus, it is possible to analyze the surface 19 of the railway wheel 5 and verify whether it has deformations, protrusions, or irregularities. This analysis 19 avoids possible accidents due to wear of the surface 3 of the wheel 5 and also ensures a greater understanding on the wheel 5/rail 4 interaction.

Having described the system and method in its preferred and alternative embodiments, it is concluded that the invention achieves its objects by a system to monitor railway wheels 5 capable of measuring the effective wear occurring in all parts of the wheel 5.

In addition, the method to monitor railway wheels 5 allows to compare a theoretical model of a new railway wheel 5 with the observed model of the monitored wheel 5, thus allowing to verify its effective wear.

The invention claimed is:

1. A system to monitor railway wheels having sides arranged in parallel, the sides including an inner side and an outer side and a surface disposed perpendicularly in a space defined between the inner side and the outer side of the railway wheel, comprising:
 a system to measure a profile of the railway wheel comprising stereo cameras, including a first stereo camera and a second stereo camera;
 a system to analyze the profile of the railway wheel based on a theoretical two-dimensional model of the railway wheel in a perfect condition; and
 a system to analyze the surface of the railway wheel based on a theoretical three-dimensional model of the railway wheel in the perfect condition,
 wherein the stereo cameras are configured to capture images of the sides of the railway wheel, the first stereo camera capturing first images of the inner side of the railway wheel and the second stereo camera capturing second images of the outer side, and
 wherein the images captured by the stereo cameras are subjected to computational processing configured to generate a first three-dimensional reconstruction of the first side and a second three-dimensional reconstruction of the second side of the railway wheel.

2. The system to monitor railway wheels according to claim 1, wherein the first three-dimensional reconstruction and the second three-dimensional are subjected to fusion by a fusion computational process, forming an observed three-dimensional model of the railway wheel.

3. The system to monitor railway wheels according to claim 2, wherein the system to analyze the profile of the railway wheel performs a mapping of the observed three-dimensional model to transform it into an observed two-dimensional model.

4. The system to monitor railway wheels according to claim 3, wherein the system to analyze the profile of the railway wheel performs an analysis of an effective wear suffered by the profile of the railway wheel based on a curve generated by a computational comparison of the profile of the observed two-dimensional model with a theoretical profile of the theoretical two-dimensional model.

5. The system to monitor railway wheels according to claim 3, wherein the system to measure the profile of the railway wheel produces a graph of a Euclidean distance provided by a computational comparison of a theoretical profile of the theoretical two-dimensional model with an observed profile of the observed two-dimensional model, the graph being configured to estimate geometrical characteristics of the profile of the rail wheel.

6. The system to monitor railway wheels according to claim 2, wherein the system to analyze the surface of the railway wheel performs an analysis of an effective wear suffered by the surface of the railway wheel based on a computational comparison of the surface of the observed three-dimensional model with the theoretical three-dimensional model.

7. The system to monitor railway wheels according to claim 6, wherein a computational comparison calculates a Euclidean distance between points belonging to the theoretical three-dimensional model and related points in the observed three-dimensional model for a region specified in a surface area of the railway wheel.

8. The system to monitor railway wheels according to claim 2, wherein the computational processing includes registration of points in a three-dimensional cloud.

9. The system to monitor railway wheels according to claim 1, wherein the stereo cameras each comprise two lenses, the first stereo camera including a first left lens and a first right lens and the second stereo camera including a second left lens and a second right lens.

10. The system to monitor railway wheels according to claim 1, wherein the stereo cameras comprise laser sensors and light projectors.

11. The system to monitor railway wheels according to claim 1, wherein the computational processing includes: acquisition of a stereo image from the stereo cameras; calibration of the stereo cameras; rectification of the stereo image; segmentation of the railway wheel; mapping and calculation of image disparity; and triangulation.

12. The system to monitor railway wheels according to claim 1, wherein the system to analyze the profile of the railway wheel and the system to analyze the surface of the railway wheel are configured to identify a wheel/rail interaction, reduce fuel consumption of a railway vehicle, increase comfort of passengers transported by the railway vehicle, and/or decrease risk of derailment of the railway vehicle.

13. A method to monitor railway wheels, comprising:
 capturing a stereo image of both sides of a railway wheel obtained by stereo cameras;
 calibrating the stereo cameras due to distortions occurring on lenses of the stereo cameras;
 segmenting the railway wheel;
 reconstructing a three-dimensional model of the both sides of the railway wheel;
 removing distorted three-dimensional points, generating greater precision in the reconstructed three-dimensional model;
 fusioning the three-dimensional points, generating an observed three-dimensional model of the railway wheel;
 mapping the observed three-dimensional model to an observed two-dimensional model;
 measuring a profile of the railway wheel;
 analyzing an observed profile of the observed two-dimensional model of the railway wheel; and
 analyzing an observed surface of the observed three-dimensional model of the railway wheel.

14. The method to monitor railway wheels according to claim 13, wherein the measuring comprises the following processes:
 identification of a set of path points;
 computation of normal vectors;
 data association comparing points of the set of path points of the observed two-dimensional model with corresponding points along the theoretical two-dimensional model; and
 estimation of characteristics of the railway wheel, configured to use the corresponding points obtained from the data association to calculate geometric characteristics of the railway wheel.

15. The method to monitor railway wheels according to claim 14, wherein the geometrical characteristics calculated by the estimation of the characteristics of the railway wheel comprise: new flange height, new flange width, new wheel width, and new flange angle.

16. The method to monitor railway wheels according to claim 13, wherein the analyzing comprises the following processes:

identifying a set of path points, configured to define all points indicated in the theoretical two-dimensional model;

data association to compare points of the set of path points of the observed two-dimensional model (A) with corresponding points along the theoretical two-dimensional model; and estimation of characteristics of the railway wheel resulting in a curve of an effective wear of the profile of the railway wheel.

17. The method to monitor railway wheels according to claim 13, wherein the analyzing is performed by dividing the observed three-dimensional model into several slices, applying a module of analysis of the theoretical two-dimensional profile, and comparing these two models for each selected slice, estimating by a difference between these two models and an effective wear suffered by the surface of the railway wheel.

18. The method to monitor railway wheels according to claim 13, wherein the analyzing is performed by corresponding pairs of three-dimensional points to points of the observed three-dimensional model and the theoretical three-dimensional model, comparing a distance of these points by algorithms.

* * * * *